US006391849B1

(12) United States Patent
Shamay et al.

(10) Patent No.: US 6,391,849 B1
(45) Date of Patent: May 21, 2002

(54) METHOD AND PHARMACEUTICAL COMPOSITION FOR DISRUPTING LACTATION IN A MAMMARY GLAND AND FOR TREATING AND PREVENTING MASTITIS (75) Inventors: Avi Shamay, Mazkeret Batia; Nissim Silanikove, Yavne, both of (IL)

(73) Assignee: Agricultural Research Organization, The Volcani Center, Bet Dagan (IL)

( * ) Notice: Subject to any disclaimer, the term of this patent is extended or adjusted under 35 U.S.C. 154(b) by 0 days.

(21) Appl. No.: 09/443,339

(22) Filed: Nov. 19, 1999

(51) Int. Cl.⁷ ......................... A61K 38/00; A61K 47/00
(52) U.S. Cl. ........................ 514/2; 514/773; 514/775
(58) Field of Search .......................... 514/2, 773, 775

(56) References Cited

U.S. PATENT DOCUMENTS 5,130,300 A * 7/1992 Collier et al. .................. 514/12

OTHER PUBLICATIONS

FitzGerald, RJ, "Potential Uses of Caseinophosphopeptides", *Int. Diary J.*, 8:451–457, 1998.
Patton,S., "Reversible Suppression of Milk Secretion by Concanavalin A", *FEBS Letters*, 71(1): 154–156, 1976.
Patton,S., Mechanisms of Secretion: Effects of Colchicine and Vincristine on Composition and Flow of Milk in the Goat, *J. Dairy Science*, 59(8): 1414–1419, 1975.
Stelwagen et al, "EGTA–induced Disruption of Epithelial Cell Tight Junctions in the Lactating Caprine Mammary Gland", Am. J. Physiol., 269:R848–R855, 1995.
Stelwagen et al, "Time Course of Milk Accumulation–Induced Opening of Mammary Tight Junctions, and Blood Clearance of Milk Components", Am. J. Physiol., 273: R379–R386, 1997.

* cited by examiner

*Primary Examiner*—Kevin E. Weddington (57) ABSTRACT

A method and pharmaceutical composition for ceasing milk production, for inducing involution, or for treating infection in a mammary gland of a lactating animal is described. The method is effected by direct administration of calcium chelators to the gland, or upon administration of enzymes which cause production of chelators in situ. The invention can be used to change the physiologic state of a single mammary gland of a lactating animal without significantly affecting the physiologic state of other mammary glands of the same animal. Changes resulting from use of the invention may be either transient or long lasting. The invention is expected to have uses in commercial agriculture and human medicine.

9 Claims, 7 Drawing Sheets

METHOD AND PHARMACEUTICAL COMPOSITION FOR DISRUPTING LACTATION IN A MAMMARY GLAND AND FOR TREATING AND PREVENTING MASTITIS

FIELD AND BACKGROUND OF THE INVENTION

The present invention relates to a method and a pharmaceutical composition for disrupting lactation in a mammary gland by reducing the concentration of extracellular divalent calcium cations in the gland, and more particularly, to the use of proteose-peptones (PPs) to accomplish this reduction. The present invention further relates to a method and a pharmaceutical composition for the treatment and prevention of mastitis by reducing the concentration of extracellular divalent calcium cations in infected glands, and more particularly to the use of proteose-peptones to accomplish this reduction.

Citation or identification of any reference in this section or in any other section of this application shall not be construed as an admission that such reference is available as prior art to the present invention.

The process of mammary gland involution in ruminants and in other mammals proceeds through several distinct stages that involve cessation of milk production, apoptosis of epithelial cells and tissue remodeling.

During the first stage, mammary involution is triggered by local stimuli that initiate apoptosis, but the process can be reversed by reinitiating milk removal (Capuco and Akers, 1999; Wilde et al., 1999). This local control can cause involution and apoptosis when milk stasis is induced in individual glands, as in lactating goats following unilateral cessation of milking (Quarrie et al., 1994), or in lactating mice by teat-sealing (Li et al., 1997; Marti et al., 1997; Quarrie et al., 1996).

The second stage of involution is persistent, and milk removal can not cause resumption of milk secretion (Capuco and Akers, 1999; Wilde et al, 1999). This stage is characterized by activation of proteases that destroy the lobular-alveolar structure of the gland by degrading the extracellular matrix and basement membrane, as well as massive loss of alveolar cells.

Cellular tight junctions (TJ) form a gasket around the apical side of each epithelial cell joined to a similar structure on adjacent cells. Intact TJ act as a barrier between the apical and basolateral side of the cell, thus preventing paracellular transport and maintaining an electrochemical gradient of up to 35 mV in the mammary gland (Fleet and Peaker, 1978; Nguyen and Neville, 1998). When milk is not continuously removed from the gland, TJ become leaky. With respect to the process of mammary gland involution, it is believed that both local factors, and systemic factors (e.g., prolactin, progesterone, and glucocorticoids) play a role in the regulation of mammary TJ (Nguyen and Neville, 1998).

Maintenance of extracellular $Ca^{+2}$ levels is essential for maintaining TJ integrity in the mammary secretory epithelium (Neville and Peaker, 1981; Pitelka et al., 1983). Although only about 7% of the total calcium in human and bovine milk is in free ionized form (Neville et al., 1994), this is apparently sufficient to maintain TJ integrity in the intact gland. Neville and Peaker (1981) and Stelwagen et al. (1995) have shown that introducing EGTA into the mammary gland induced transient loss of TJ integrity and transient reduction of milk yield, by acting as a chelator of ionized calcium. The major native proteolytic activity in bovine milk is from the serine protease plasmin and its zymogen (Andrews, 1983). There is evidence suggesting that the plasmin activator (PA)-plasminogen-plasmin system is involved in control of milk secretion and tissue remodeling during involution (Osowski et al., 1979; Politis, 1996).

Proteose-peptones (PPs), also known as caseinophosphopeptides, a group of boiling-resistant peptides constituting about a third of whey proteins, are principally the products of the activity of plasmin on β-casein and alpha-s1- and alpha-s2-casein (Andrews, 1983). Based on point of cleavage of casein moieties by plasmin, about 50% of the protease peptones in whey are phosphopeptides (Anderson et al., 1995). Caseinophosphopeptides have been shown to possess the unique property of being able to bind macroelements such as Ca, Mg, and Fe, along with trace elements such as Zn, Ba, Cr, Ni, Co and Se. One mole of caseinophosphopeptide may bind 20 to 40 mole of Ca, 17 mole of phosphate and 6 mole of Zn (Anderson et al., 1995; Fitzgerald, 1998).

Current management of dairy cows and goats results in significant overlap of lactation and pregnancy, such that these animals are typically pregnant when milking is terminated during late lactation. When milk stasis occurs, the mammogenic and lactogenic stimulation of pregnancy opposes stimuli for mammary involution (Capuco and Akers, 1999). This causes involution of the mammary gland to occur at a slower rate and alveolar structure to be maintained for a greater period of the involution process in dairy cows and goats (Capuco and Akers, 1999; Wilde et al., 1999) than in sheep (Tatarczuch et al., 1997) and rodents (Li et al., 1997).

By accelerating the natural appearance of a local factor which is responsible for inducement of involution, it is possible to override the anti-involution systemic stimuli, and to accelerate the process and extent of involution. Such a capacity to manipulate the process of involution has a great potential to increase animal productivity by enhancing the capacity to control mastitis (Olivier and Sordillio, 1989), and increasing the potential of the cows to produce milk (Capuco and Akers, 1999).

While it is known that milk contains antibiotic/host protective peptides such as casecidin and isracidin (for review see Lahov and Regelson, Food-Chem-Toxicol. (1996) 34(1): 131–45), with apparent efficacy in preventing or reversing infection in livestock animals, the present invention deals with a chemically distinct group of peptides.

Controlling economic losses associated with mastitis in the dairy industry has long been considered the most important single factor in achieving profitability. The increasing prevalence of antibiotic resistant bacteria in the field has made this control increasingly difficult to achieve. Deployment of BST (Bovine Somatotropin) in the milking herd, while increasing overall milk yield, has also contributed to difficulties in controlling mastitis. In many cases, herdsmen must remove high producing animals from the milking herd prior to their scheduled withdrawal in order to treat infection. In addition, mastitis may persist from one lactation cycle to the subsequent one, necessitating the permanent removal of otherwise valuable animals from the milking herd.

There is thus a widely recognized need for, and it would be highly advantageous to have, a method and a pharmaceutical composition to transiently or persistently accelerate the process of involution in one or more glands of a lactating animal. There is also a widely recognized need for, and it would be highly advantageous to have, a method and a pharmaceutical composition for the treatment or prevention of mastitis.

SUMMARY OF THE INVENTION

According to one aspect of the present invention there is provided a method of ceasing milk production in a mammary gland of a lactating animal, the method comprising the step of administering a chelating agent into the mammary gland of the lactating animal.

According to another aspect of the present invention there is provided a method of inducing involution in a mammary gland of a lactating animal, the method comprising the step of administering a chelating agent into the mammary gland of the lactating animal.

According to yet another aspect of the present invention there is provided a method of treating an infection in a mammary gland of a lactating animal, the method comprising the step of administering a chelating agent into the mammary gland of the lactating animal.

According to still another aspect of the present invention there is provided a pharmaceutical composition for ceasing milk production in a mammary gland of a lactating animal, the pharmaceutical composition comprising, as an active ingredient, an effective amount of a chelating agent and a pharmaceutically acceptable carrier.

According to an additional aspect of the present invention there is provided a pharmaceutical composition for inducing involution in a mammary gland of a lactating animal, the pharmaceutical composition comprising, as an active ingredient, an effective amount of a chelating agent and a pharmaceutically acceptable carrier.

According to yet an additional aspect of the present invention there is provided a pharmaceutical composition for treating an infection in a mammary gland of a lactating animal, the pharmaceutical composition comprising, as an active ingredient, an effective amount of a chelating agent and a pharmaceutically acceptable carrier.

According to further features in preferred embodiments of the invention described below, the step of administering the chelating agent into the mammary gland of the lactating animal is effected by injecting the chelating agent into a teat canal of the mammary gland of the lactating animal.

According to still further features in the described preferred embodiments, the chelating agent is selected from the group of chelating agents consisting of casein derived proteose-peptones, synthetic phosphopeptides.

According to still further features in the described preferred embodiments, dosing and repetition of the step of administering the chelating agent into the mammary gland of the lactating animal are selected so as to transiently cease milk production in the mammary gland of the lactating animal.

According to still further features in the described preferred embodiments, dosing and repetition of the step of administering the chelating agent into the mammary gland of the lactating animal are selected so as to cause persistent cessation of milk production in the mammary gland of the lactating animal.

According to still further features in the described preferred embodiments, a single dose of protease-peptone in combination with cessation of milking will induce involution and will result in persistent cessation of milk production in the mammary gland of the lactating animal.

According to still further features in the described preferred embodiments, dosing and repetition of the step of administering the chelating agent into the mammary gland of the lactating animal, or a single dose of the chelating agent combined with ceasing of milking are selected so as to cause persistent cessation of milk production in the mammary gland of the lactating animal.

According to still further features in the described preferred embodiments, the animal is a livestock animal.

According to still further features in the described preferred embodiments, the animal is selected from the group of animals consisting of cow, goat, sheep, lama, human, camel, donkey, pig, dog and cat.

According to still further features in the described preferred embodiments, dosing and repetition of the step of administering the chelating agent into the mammary gland of the lactating animal are selected so as cause involution in the mammary gland of the lactating animal which is reversible by ceasing treatment.

According to still further features in the described preferred embodiments, dosing and repetition of the step of administering the chelating agent into the mammary gland of the lactating animal are selected so as cause involution in the mammary gland of the lactating animal which is persistent after ceasing treatment.

According to still further features in the described preferred embodiments, dosing and repetition of the step of administering said chelating agent into the mammary gland of the lactating animal are selected so as to cause involution similar to that which occurs at the end of a lactation cycle in the mammary gland of the lactating animal.

According to yet an additional aspect of the present invention there is provided a method for reducing the amount of free ionic calcium in milk within a lactating mammary gland, the method comprising the steps of (a) administering a proteolytic enzyme into a teat canal, so as to produce at least one proteose peptone by digestion of a substrate within the milk, so as to chelate the free ionic calcium.

According to another additional aspect of the present invention there is provided a pharmaceutical composition for reducing the amount of free ionic calcium in milk within a lactating mammary gland comprising an effective amount of a proteolytic enzyme capable of digesting at least one milk protein so that at least one proteose peptone capable of chelating the free ionic calcium in the milk is formed, and a pharmaceutically acceptable carrier.

The present invention successfully addresses the shortcomings of the presently known configurations by providing methods of ceasing lactation, causing involution, and treating infection in individual mammary glands of lactating animals without disturbing lactation in remaining glands of the same animal. This allows high producing animals to remain in the herd during treatment. In addition, pharmaceutical compositions provided as part of the present invention reduce the dependence of herdsmen on antibiotics to treat infection, alleviating both the problem of antibiotic resistant mastitic infections, and the perceived problem of widespread agricultural use of antibiotics as a cause of antibiotic resistance in bacteria which infect humans. As a further benefit, the present invention will successfully overcome the problem of persistence of mastitic infection from one lactation cycle to the next. Therefore the present invention is recommended for routine prophylactic use when drying lactating animal.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show details of the invention in more detail than is necessary for a fundamental understanding of the invention, the description taken with the drawings making apparent to those skilled in the art how the several forms of the invention may be embodied in practice.

In the drawings:

FIG. 2a' shows levels of total calcium as a function of time post treatment, in the milk of animals that received multiple treatment with PPs which were injected to the teat canal of both udders after milking for five milkings. Arrow indicates day of initiation of treatment.

FIG. 2b' shows levels of free calcium cations as a function of time post treatment, in the milk of animals that received multiple treatment with PPs in both glands. Injections were given in the teat canal after milking five milkings. Arrow indicates first day of treatment.

FIG. 2c' shows levels of bound calcium as a function of time post treatment, in the milk of animals that received multiple treatment with PPs in both glands in the milk of animals that received multiple treatment with PPs in both glands. Injections were given in the teat canal after milking for five milkings. Arrow indicates first day of treatment.

FIG. 2d' shows levels of citrate-calcium as a function of time post treatment, in the milk of animals that received multiple treatment with PPs in both glands. Injections were given in the teat canal after milking for five milkings. Arrow indicates first day of treatment.

FIG. 3a' shows serum albumin concentration as a function of time post treatment, in milk of animals that received multiple treatment with PPs in both glands. Injections were given in the teat canal after milking for five milkings. Arrow indicates first day of treatment.

FIG. 3b' shows lactose concentration as a function of time post treatment, in milk of animals that received multiple treatment with PPs in both glands. Injections were given in the teat canal after milking for five milkings. Arrow indicates first day of treatment.

FIG. 3c' shows potassium ion concentration as a function of time post treatment, in milk of animals that received multiple treatment with PPs in both glands. Injections were given in the teat canal after milking for five milkings. Arrow indicates first day of treatment.

FIG. 3d' shows potassium ion concentration as a function of time post treatment, in milk of animals that received multiple treatment with PPs in both glands. Injections were given in the teat canal after milking for five milkings. Arrow indicates first day of treatment.

FIG. 4a' shows total protein level, in the milk of PPs treated glands (multiple treatment, both glands as a function of time post treatment. Injections were given in the teat canal after milking for five milkings. Arrow indicates first day of treatment.

FIG. 4b' shows casein level, in the milk of PPs treated glands (multiple treatment, both glands), as a function of time post treatment. Injections were given in the teat canal after milking for five milkings. Arrow indicates first day of treatment.

FIG. 4c' shows whey level, in the milk of PPs treated glands (multiple treatment, both glands), as a function of time post treatment. Injections were given in the teat canal after milking for five milkings. Arrow indicates first day of treatment.

FIG. 4d' shows protease peptone level as a function of time post treatment, in the milk of PPs treated glands (multiple treatment, both glands. Injections were given in the teat canal after milking for five milkings. Arrow indicates first day of treatment.

FIG. 5a' shows plasmin level, in the milk of PPs treated glands (single treatment, single gland per animal), as a function of time post treatment. Control values (non treated glands) are indicated by diamond shape. Experimental values are indicated by squares. Time zero is treatment day.

FIG. 5b' demonstrate plasmin level in the milk of PPs treated glands (multiple treatment, both glands), as a function of time post treatment. Injections were given in the teat canal after milking for five milkings. Time zero indicates first day of treatment.

DESCRIPTION OF THE PREFERRED EMBODIMENTS

The present invention is of a method which can be used to cease milk production, to induce involution, or to treat infection in a mammary gland of a lactating animal. The present invention is further of pharmaceutical compositions employed in order to cease milk production, to induce involution, or to treat infection in a mammary gland of a lactating animal. Specifically, the present invention can be used to change the physiologic state of a single mammary gland of a lactating animal without significantly affecting the physiologic state of other mammary glands of the same animal. The present invention is expected to have uses in commercial agriculture and human therapy.

The principles and operation of a method which can be used to cease milk production, to induce involution, or to treat infection in a mammary gland of a lactating animal according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For purposes of this specification and the accompanying claims a "persistent cessation of milk production" refers to interruption in lactation which is reversible only by pregnancy, by hormonal treatment or is irreversible altogether.

For purposes of this specification and the accompanying claims a "permanent" refers to a condition which persists until initiation of pregnancy or a hormonal treatment which mimics pregnancy.

For purposes of this specification and the accompanying claims a "permanent" refers to a condition which persists until initiation of pregnancy or a hormonal treatment which mimics pregnancy.

Figure 1A:
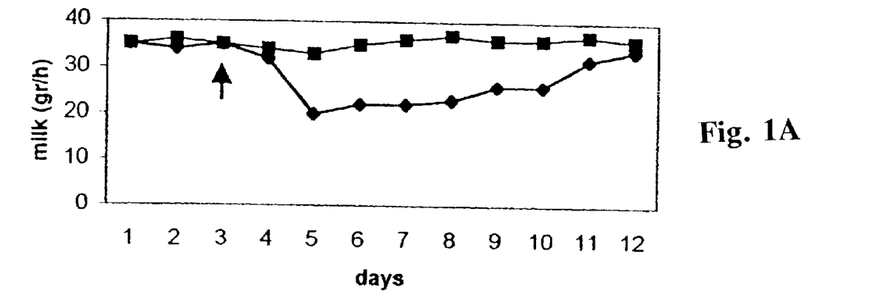
FIG. 1a shows milk secretion in grams/hr before and after PPs treatment of mammary glands. PPs was injected to the teat canal of the left udder after milking. Arrow indicates day of the single treatment. Control values (non treated gland) are indicated by squares. Experimental values are indicated by diamond shape.

As further detailed in the examples section that follows, FIG. 1a illustrates the transient effect on milk yield in a single mammary gland of a lactating goat in response to a single injection of a PPs solution. Injection of the PPs solution into the teat canal on day 3 causes a sharp decline in milk production beginning on day 4 followed by a gradual return to full lactation capacity on day 12. Since milk yield in the opposite gland (FIG. 1a) remains unaffected, the mechanism of action is judged to be local, and not systemic. This fact is important because it means that milk from the untreated gland should have normal composition and also be suitable for consumption. This data shows a preferred embodiment for a method of ceasing milk production, in this case reversibly. The injected proteose peptones embody a pharmaceutical composition for ceasing milk production.

Repeated administration of PPs to a single gland (FIG. 1b) causes that gland to cease lactating, as if milking had been stopped. The opposite gland in the same animal shows no significant change in milk production. In terms of commercial practice, this allows a herdsman to keep a mastitic animal in production and receive a partial yield in a case where infection would have previously dictated removal of that animal from production altogether. These data represent embodiments of methods for ceasing milk production and for causing involution. These effects are reversible at this stage only by pregnancy or by hormonal treatments which mimic pregnancy. Similarly, the proteose peptones administered embody a pharmaceutical composition for causing persistent cessation of milk production and for causing involution.

Figure 1B:
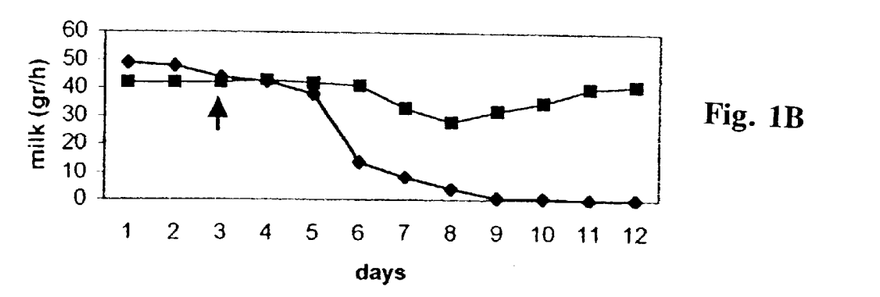
FIG. 1b shows milk secretion in grams/hr before and after PPs treatment of mammary glands. PPs were injected to the teat canal of the left udder after milking for five milkings. Arrow indicates day of initiation of treatment. Control values (non treated gland) are indicated by squares. Experimental values are indicated by diamond shape.
Figure 1C:
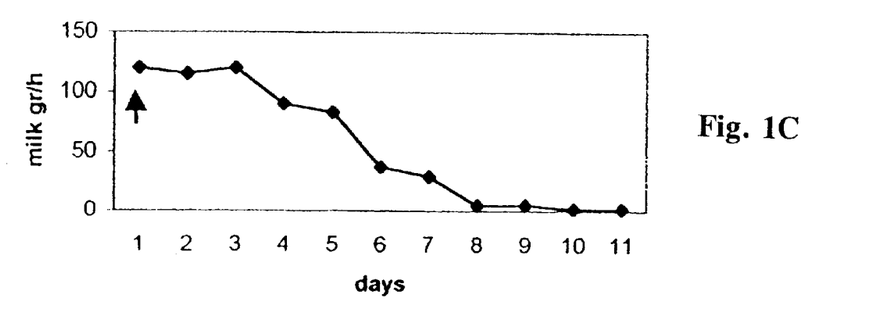
FIG. 1c shows milk secretion in grams/hr before and after PPs treatment of mammary glands. PPs were injected to the teat canal of the left udder after milking for five milkings. Arrow indicates day of initiation of treatment. Control values (non treated animal) are indicated by squares. Experimental values are indicated by diamond shape.

FIG. 1c shows that multiple PPs treatment of both glands of a lactating animal can effectively cease lactation, in much the same way that cessation of milking normally does. Involution occurs subsequent to cessation of lactation. These data represent embodiments of methods for permanently ceasing milk production and for causing involution. Similarly, the protease peptones administered embody a pharmaceutical composition for permanently ceasing milk production and for causing involution. These data show that the present invention may be used either on a subset of the mammary glands of a lactating animal, or on all the mammary glands.

Without limiting the scope of the present invention, it is believed, and supported by experimental results, that the mechanism of action of the observed reduction in lactation output is apparently a reduction of free calcium ion concentration in milk within mammary alveoli to below 2 millimolar (FIG. 2b) in response to PPs injection. Repeated injections of PPs, which keep the level of free calcium ions below this 2 millimolar level lead to physical changes within the gland known as involution. The involution process, once completed, is reversible only by pregnancy or by a hormonal treatment which mimics pregnancy. Alternately, a single injection combined with cessation of milking can be employed to accelerate the involution process by rapidly reducing the level of free calcium ions in the milk.

Figure 3A:
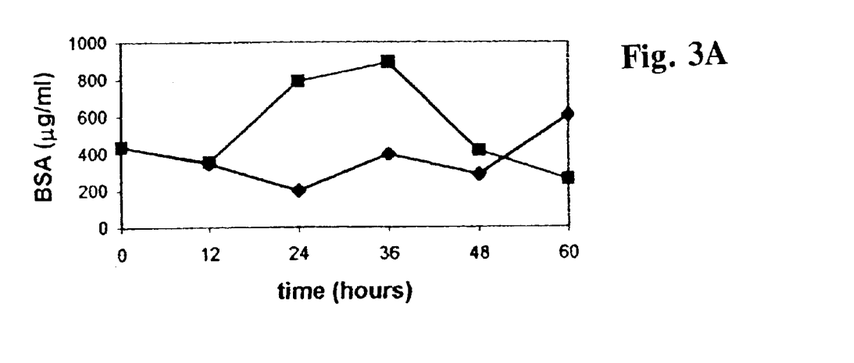
FIG. 3a shows serum albumin concentration, in milk of a gland treated one time with PPs at time 0, as a function of time post treatment. Control values (non treated gland) are indicated by diamond shape. Experimental values are indicated by squares.
Figure 3B:
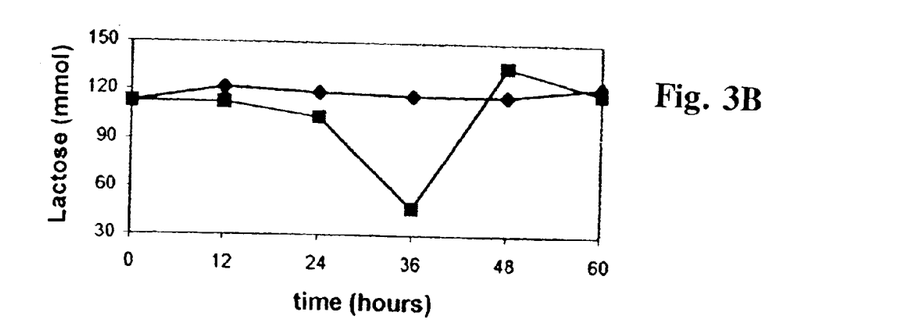
FIG. 3b shows lactose concentration, in milk of a gland treated one time with PPs at time 0, as a function of time post treatment. Control values (non treated gland) are indicated by diamond shape. Experimental values are indicated by squares.
Figure 3C:
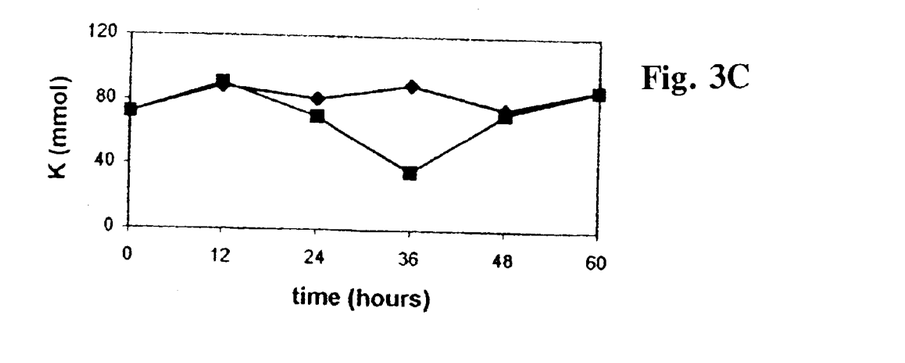
FIG. 3c shows potassium ion concentration, in milk of a gland treated one time with PPs at time 0, as a function of time post treatment. Control values (non treated gland) are indicated by diamond shape. Experimental values are indicated by squares.
Figure 3D:
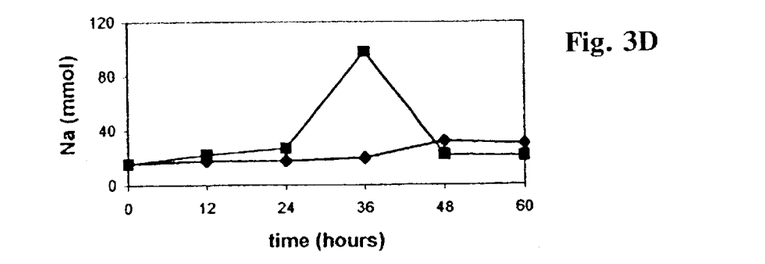
FIG. 3d shows sodium ion concentration, in milk of a gland treated one time with PPs at time 0, as a function of time post treatment. Control values (non treated gland) are indicated by diamond shape. Experimental values are indicated by squares.
Figure 4A:
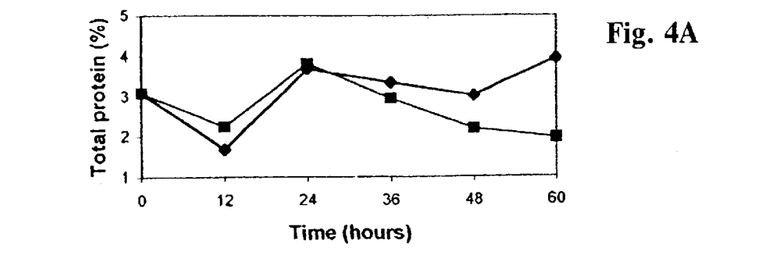
FIG. 4a shows total protein level, in the milk of PPs treated glands (single treatment, single gland per animal), as a function of time post treatment. Control values (non treated glands) are indicated by diamond shape. Experimental values are indicated by squares. % indicates grams/100/ml.
Figure 4B:
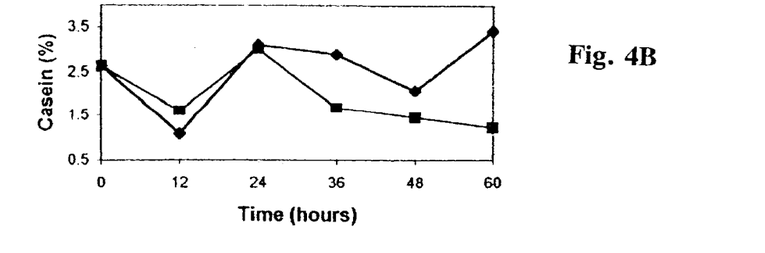
FIG. 4b shows total casein level, in the milk of PPs treated glands (single treatment, single gland per animal), as a function of time post treatment. Control values (non treated glands) are indicated by diamond shape. Experimental values are indicated by squares. % indicates grams/100/ml.
Figure 4C:
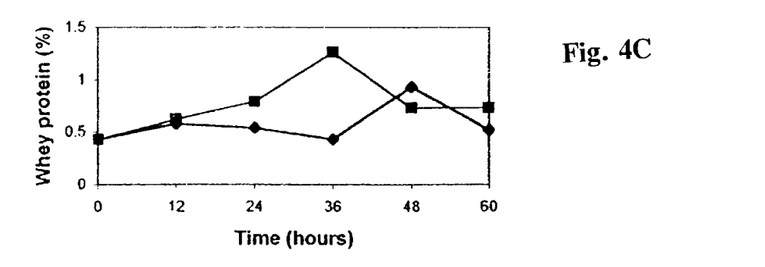
FIG. 4c shows total whey protein level, in the milk of PPs treated glands (single treatment, single gland per animal), as a function of time post treatment. Control values (non treated glands) are indicated by diamond shape. Experimental values are indicated by squares. % indicates grams/100/ml.
Figure 4D:
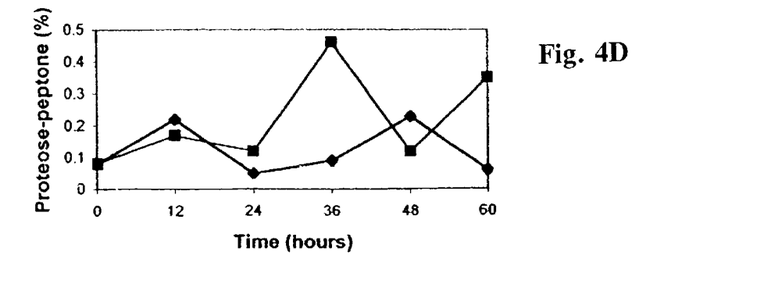
FIG. 4d shows total proteose peptone level, in the milk of PPs treated glands (single treatment, single gland per animal) as a function of time post treatment. Control values (non treated glands) are indicated by diamond shape. Experimental values are indicated by squares. % indicates grams/100/ml.
Figure 5A:
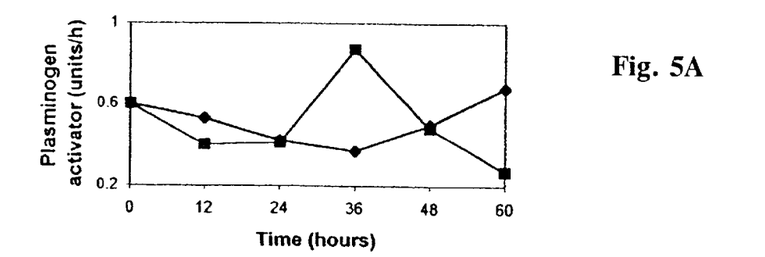
FIG. 5a shows plasminogen activator level, in the milk of PPs treated glands (single treatment, single gland per animal), as a function of time post treatment. Control values (non treated glands) are indicated by diamond shape. Experimental values are indicated by squares. Time zero is treatment day.
Figure 5B:
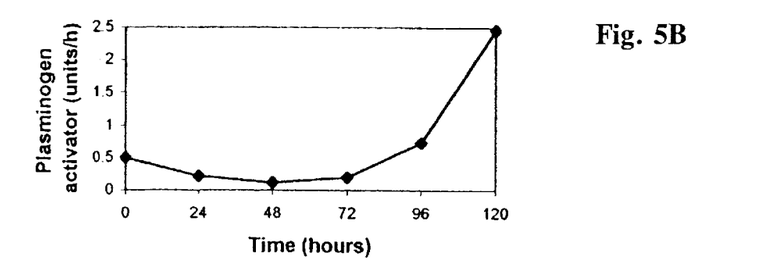
FIG. 5b demonstrate plasminogen activator level, in the milk of PPs treated glands (multiple treatment, both glands), as a function of time post treatment. Injections were given in the teat canal after milking for five milkings. Time zero indicates first day of treatment.

Concurrent with the reduction in lactation output are changes in the composition of the secreted fluid in terms of serum albumin, lactose, potassium and sodium (FIG. 3) as well as total protein, whey protein, casein protein and protease peptone level (FIG. 4). These changes describe a transition from normal milk to a substance more closely resembling serum or colostrum. Such a change is indicative of disruption of cellular tight junctions, a conclusion supported by the increased levels of plasminogen activator and plasmin in response to PPs treatment (FIG. 5). Plasmin leakage from the interstitial fluid into the milk containing alveoli causes increased production of PPs from caseins (FIG. 4d) leading to increased weakening of cellular tight junctions. Apparently, this process becomes self sustaining if free calcium ion levels in milk remain below 2 mM for more than approximately 72 hours.

In the case of infection of the teat (mastitis), this leakiness of tight junctions allows immunoglobulins to enter the alveolar space and combat the infection. In some cases, infection may be eradicated while a return to lactation is still feasible in the gland in question. In other cases, sacrifice of production from the infected gland for the remainder of the lactation cycle may be necessary to salvage production from the remaining glands. Experimental support for preferred embodiments that deal with methods and pharmaceutical compositions for treating mammary gland infections are presented in example 4 which describes treatment of mastitis in a single udder of each of five cows. This experimental data shows reduction to practice of both methods and pharmaceutical compositions for treating infection of a mammary gland.

According to alternative preferred embodiments of the present invention, reducing the amount of free ionic calcium in milk within a lactating mammary gland can be effected by administering a proteolytic enzyme, or a pharmaceutical composition containing same, into a teat canal so that it can digest one or more endogenous milk proteins thereby producing protease peptones. These PPs would subsequently chelate the free ionic calcium and cause a physiologic response similar to the response described hereinabove for direct administration of PPs. This embodiment encompasses the same applications as direct administration of PPs, namely cessation of lactation, whether transient or persistent, involution and treatment of infection.

According to alternative preferred embodiments of the present invention, administration of the chelating agent into the mammary gland of the lactating animal is effected by injecting the chelating agent into a teat canal.

Although experimental data presented in the Examples section hereinbelow describes results achieved with casein derived protease peptones.

According to alternative preferred embodiments of the present invention, the chelating agent is selected from the group of chelating agents consisting of casein derived proteose-peptones, synthetic or purified phosphopeptides, such as, for example, one or more of those proteose peptones listed in SEQ ID NOs: 1–7, derived either by protein digestion or by chemical (e.g., solid phase) synthesis.

According to alternative preferred embodiments of the present invention, dosing and repetition of the administration of the chelating agent into the mammary gland are selected so as to transiently cease milk production in the mammary gland.

According to alternative preferred embodiments of the present invention, dosing and repetition of the administration of the chelating agent into the mammary gland of the lactating animal are selected so as to cause persistent cessation of milk production in the mammary gland of the lactating animal.

According to alternative preferred embodiments of the present invention, the animal is a livestock animal.

According to alternative preferred embodiments of the present invention, the animal is selected from the group of animals consisting of cow, goat, sheep, lama, human, camel, donkey, pig, dog, and cat.

According to alternative preferred embodiments of the present invention, dosing and repetition of the administration of the chelating agent into the mammary gland of the lactating animal are selected so as cause partial involution in the mammary gland of the lactating animal which is reversible by ceasing treatment.

According to alternative preferred embodiments of the present invention, dosing and repetition of the administration of the chelating agent into the mammary gland of the lactating animal are selected so as cause complete involution in the mammary gland of the lactating animal which persists also after ceasing treatment.

According to alternative preferred embodiments of the present invention, dosing and repetition of administration of the chelating agent into the mammary gland are selected so as to cause involution similar to that which occurs at the end of a lactation cycle.

According to several aspect of the present invention there is provided a pharmaceutical composition comprising, as an active ingredient, a calcium ions chelator or a protease and a pharmaceutically acceptable carrier. The chelator according to the present invention can be administered to an organism per se, or in a pharmaceutical composition where it is mixed with suitable carriers or excipients.

As used herein a "pharmaceutical composition" refers to a preparation of a chelator or protease as described herein, with other chemical components such as physiologically suitable carriers and excipients. The purpose of a pharmaceutical composition is to facilitate administration of a compound to an organism.

Herein the term "active ingredient" refers to a compound accountable for the biological effect.

Herein, the terms "physiologically acceptable carrier" and "pharmaceutically acceptable carrier" which may be interchangeably used refer to a carrier or a diluent that does not cause significant irritation to an organism and does not abrogate the biological activity and properties of the administered chelator.

Herein the term "excipient" refers to an inert substance added to a pharmaceutical composition to further facilitate administration of a compound. Examples, without limitation, of excipients include various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredient into preparations which, can be used pharmaceutically. Proper formulation is dependent upon the route of administration chosen.

For injection, the chelators or proteases of the invention may be formulated in aqueous solutions, preferably in physiologically compatible buffers such as Hank's solution, Ringer's solution, or physiological saline buffer.

The preparations described herein may be formulated for parenteral (intra mammary) administration, e.g., by bolus injection or continuos infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the chelators or proteases in water-dispersed form. Additionally, suspensions of the active compounds may be prepared as appropriate oily injection suspensions. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility or dispersity of the chelators or proteases to allow for the preparation of highly concentrated solutions.

Alternatively, the active ingredient may be in powder form for constitution with a suitable vehicle, e.g., sterile, pyrogen-free water, before use.

Pharmaceutical compositions suitable for use in context of the present invention include compositions wherein the active ingredients are contained in an amount effective to achieve the intended purpose. More specifically, a therapeutically effective amount means an amount effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any preparation used in the methods of the invention described herein, the therapeutically effective amount or dose can be estimated initially in animal models to achieve an effective circulating concentration. Such information can be used to more accurately determine useful doses in humans or other animals.

Toxicity and therapeutic efficacy of the compounds described herein can be determined by standard pharmaceutical procedures in experimental animals. The data obtained from these and animal studies can be used in formulating a range of dosage for use in human or other animals. The dosage may vary depending upon the dosage form employed and the route of administration utilized. The exact formulation, route of administration and dosage can be chosen by the individual physician or veterinary in view of the patient's or animal condition. (See e.g., Fingl, et al., 1975, in "The Pharmacological Basis of Therapeutics", Ch. 1 p. 1).

It is noted that, in the case of local administration or selective uptake, the effective local concentration of the drug may not be related to plasma concentration. In such cases, other procedures known in the art can be employed to determine the effective local concentration.

Depending on the severity and responsiveness of the condition to be treated, dosing can also be a single administration, or with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician or veterinary, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non-limiting fashion. Generally, the nomenclature used herein and the laboratory procedures described below are those well known and commonly employed in the art. Generally enzymatic reactions are performed according to the manufacturers' specifications. General references are provided throughout this document. The procedures therein are believed to be well known in the art and are provided for the convenience of the reader. All the information contained therein is incorporated herein by reference.

Materials and Methods

Animals:

Goats: Eight multiparous (second lactation and above) lactating British Saanen goats were used. The goats about 70 kg each were held in the institute experimental goat dairy farm under continuous veterinary supervision and were disease free.

Cows: Lactating Holstein cows from the institute dairy parlor (3) and from commercial dairy farms (5) were employed. The cows were diagnosed as mastitic due to *Actinomyces pyogenes* infection. The cows were treated by a vet with PPs prepared by the inventors as described hereinbelow. Treatment schedule is described hereinbelow. A week after the treatment the udder was examined by the vet for recovery from the inflammation and udder fluid samples were taken for somatic cell count and presence of bacteria in the udder.

Preparation of proteose-peptones (PP): Fresh milk was defatted by centrifugation and digested with trypsin (500 U/L) for 4 hours at 37 degrees C. The milk was acidified to pH 4.7 with HCl and the non-digested casein was pelleted by centrifugation. The supernatant, containing the whey, was boiled for 1 hours, cooled to room temperature and neutralized to pH 7. Serum albumin and the denatured proteins after boiling were removed by centrifugation (Andrews 1978). The supernatant was sterilized with a 2.2 micron sterile filter and kept frozen until use. In addition PP can be prepared from commercial casein by dissolving 20g casein in 1 L of 50 mM Tris pH=8 or, in adding 5–10 gram of commercial casein to 1 liter defated fresh milk and continue the procedure as described above.

PP injection: PP was injected to the teat canal after milking. Injection was accomplished with a 19 gauge rounded plastic needle. The concentration of the PP was 1 mg/ml and the injected volume was 20 ml in goats and 40 ml in cows so that a total of 20 mg was delivered in each injection in goats and 40 mg in cows.

The schedule of the treatment included 5 subsequent injections of 40 ml PPs (20 mg protein/ml) into the infected gland after udder emptying at 8 hours interval Determination of milk composition: Milk samples were defatted by centrifugation at 6,000×g for 10 minutes at room temperature. Protein concentration in milk was determined by the Bradford method with a commercial reagent (Sigma, Rehovot Israel). A portion of each milk sample was acidified with HCl to pH 4.7 and then centrifuged at 22,000×g for 5 minutes at room temperature. Protein concentration in the resultant supernatant was defined as whey protein. The difference between the protein content of the defatted milk and whey protein was defined as casein. The concentrations of sodium, potassium, calcium, magnesium and phosphorus were determined by Inductively Coupled Plasma—Atomic Emission Spectrometer (Spectro, Germany). Ionized calcium in the milk was determined by a calcium electrode of Radiometer (Radiometer, Cedex, France).

Experimental Results

Example 1

Milk Production Declines as a Result of PP Injection into the Lactating Mammary Gland After injection of PP to the teat as described hereinabove, milk secretion declined by 40% relative to pretreatment data. In cases where a single gland was treated once, the parallel contralateral gland remained unaffected (FIG. 1a). In the single treated gland, the depression in milk secretion was transient, and took 7 days for complete recovery. Six treatments of a single gland after each milking. caused milk secretion in the treated gland to decline at an accelerated rate and after 94 hours only a few milliliters of milk could be harvested from the gland (FIG. 1b). The pattern of decline of milk secretion in a goat in which both glands were treated with PPs was similar to the one recorded in a single treated gland (FIG. 1c). These results indicate that a single treatment with PP can cause a transient, reversible, cessation of milk production, but that repeated treatments cause an irreversible cessation of lactation. The effect is shown to be local, and not systemic.

Example 2

Milk Composition Following a Single Dose of PP

Figure 2A:
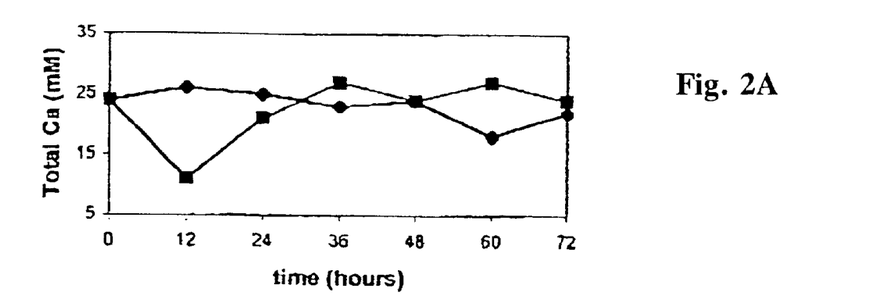
FIG. 2a shows level of total calcium in milk of a gland treated one time with PPs at time 0, as a function of time post treatment. Control values (non treated gland) are indicated by diamond shape. Experimental values are indicated by squares.
Figure 2B:
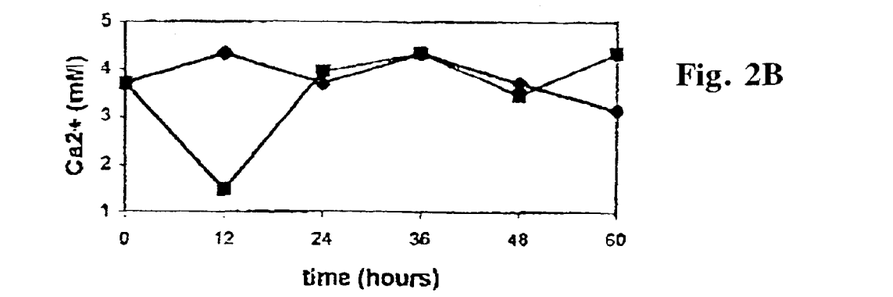
FIG. 2b shows level of free calcium cations in milk of a gland, treated one time with PPs at time 0, as a function of time post treatment. Control values (non treated gland) are indicated by diamond shape. Experimental values are indicated by squares.
Figure 2C:
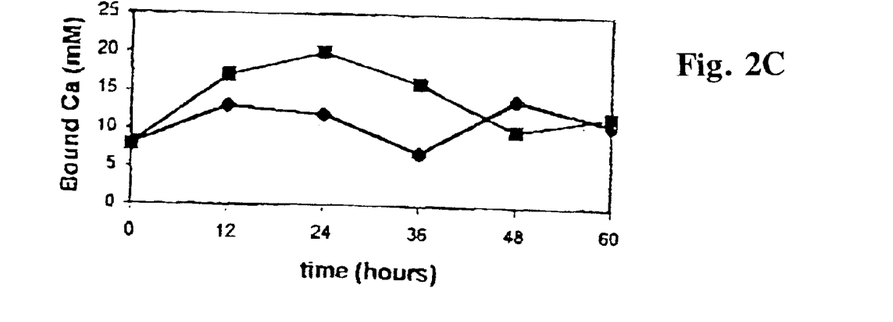
FIG. 2c shows level of bound calcium in milk of a gland, treated one time with PPs at time 0, as a function of time post treatment. Control values (non treated gland) are indicated by diamond shape. Experimental values are indicated by squares.
Figure 2D:
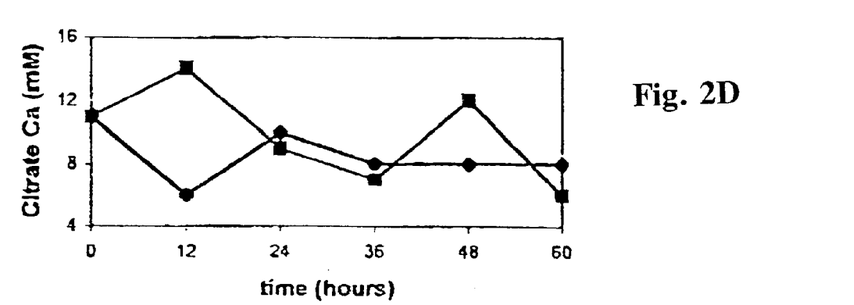
FIG. 2d shows level of citrate-Calcium in milk of a gland, treated one time with PPs at time 0, as a function of time post treatment. Control values (non treated gland) are indicated by diamond shape. Experimental values are indicated by squares.

Determination of the concentration of various milk components after a single injection of PP to the teat canal was conducted. Following the first milking 12 hours subsequent to the injection, a sharp decline in the total (FIG. 2a) and ionized (FIG. 2b) concentrations of Ca in milk was observed. This effect was transient, and at 24 hours post-treatment the total and ionized Ca concentrations in the milk returned to the pretreatment values. Bound calcium (FIG. 2c), citrate calcium (FIG. 2d) and casein (FIG. 4b) did not change significantly compared to the pretreatment values in the single dose experiment At 36 hours post-treatment, the concentration of lactose and $K^+$ (FIGS. 3b and 3c, respectively) dropped sharply, concurrent with an increase in $Na^+$ concentration (FIG. 3d). The concentration of these metabolites returned to pretreatment values after 48 hours. The pattern of changes in the concentration of BSA (FIG. 3a), whey protein (FIG. 4c), and PPs (FIG. 4d), plasminogen activator (FIG. 5a) and plasmin (FIG. 5a') activities was similar to that described for $Na^+$, except that in the case of BSA, PPs, plasminogen activator and plasmin the increase in concentration, or activities was apparent after 24 hours. Together, these changes indicate that the secreted material becomes more similar to serum and less similar to milk for a brief period following treatment.

Example 3

Milk Composition Following Multiple Doses of PP

Determination of the concentration of various milk components in response to multiple injections of PP to the teat canal was conducted. Beginning 24 hours post-treatment, the concentration of total calcium declined steadily, and stabilized after 96 hours at 6 mM, a value which was 4 times lower then the pretreatment value (FIG. 2a'). The pattern of changes in total magnesium and phosphorus was similar to that of total calcium (data not shown). Magnesium concentration was stabilized after 96 hours at 2 mM, and that of phosphorus at 7 mM, these values were 3 (magnesium) and 4 (phosphorus) time lower then the pretreatment values. A drop in $Ca^{+2}$ concentration was apparent after the first milking (12 hours post-treatment), and its concentration declined steadily, and stabilized after 96 hours at 0.6 mM, a value which was 5 time lower then the normal-pretreatment value (FIG. 2b'). The concentration of Ca bound to casein increased up to 48 hours post-treatment, and then steadily declined stabilizing after 96 hours at 3 mM, a value which was 4 time lower then the pretreatment value (FIG. 2c'). Ca bound to citrate dropped sharply from 24 hours post-treatment to 48 hours post-treatment and stabilized after 96 hours at 1.5 mM, a value which was 6 time lower then the pretreatment value (FIG. 2d'). The concentration of lactose after 48 hours post-treatment dropped sharply in comparison to the pretreatment level (FIG. 3b'). Its concentration continued to decline steadily, and by 72 hours post-treatment lactose concentration was below 1 mM. Total protein concentration was stable up to 72 hours post-treatment, and then increased sharply and steadily indicating that TJ integrity had been compromised. At 120 hours post-treatment total protein concentration was 3 times higher then the normal value (FIG. 4a'). The concentration of casein after 24 hours post-treatment dropped sharply reaching at 72 hours post-treatment a value which was 2.5 lower than the pretreatment value (FIG. 4b'). Casein concentration subsequently increased sharply and steadily in parallel to the increase in total protein (FIG. 4b'). This apparent increase was artifactual, being caused by the enormous number of mammary cells sloughed the gland cistern. These cells released many proteins which were precipitated at pH 4.6, causing them to be measured incorrectly as casein. The concentration of whey protein and PPs increased steadily after 24 hours post-treatment, and at 120 hours post-treatment their concentration was greater than 4 times the pretreatment values (FIGS. 4c' and 4d').

Serum albumin concentration began to rise 24 h after treatment and it reached typical plasma level (1500 μg/ml) after 96 hours (FIG. 3a') Sodium concentration increased sharply at some stage between 24 to 48 h after treatment and typical plasma level concentration was attained after 48 h. (FIG. 3d'). Potassium concentration dropped sharply at some stage 24 to 48 h after treatment and after 48 h it reached values slightly higher than the typical plasma levels (FIG. 3c').

Plasmin activity transiently increased at 36 hours post-treatment (single treated gland, FIG. 5a'), and at 48 hours post-treatment in the multiple treated gland, which was 4 times greater then pretreatment level (FIG. 5b'). After 72 hours, both plasmin activator, and plasmin activities rose sharply reaching at 120 hours post-treatment to levels which were 5 (plasmin activator, FIG. 5b), and 40 times (plasmin, FIG. 5b') greater then the pretreatment level.

The results of the single treatment experiment demonstrate that the PPs administered to the udders transiently induced an immediate drop in Ca concentration which was sustained for at least 12 h. This drop in calcium ion concentration induced a transient disruption of the TJ integrity which was associated with a transient drop of milk production for 7 days.

The results of the multiple treatment experiment demonstrate that maintaining $Ca^{+2}$ under 2 mM for 48 hours induced irreversible involution. This was reflected in dramatic changes in the appearance and the composition of the fluid secreted into the lumen of the gland. This fluid more closely resembled serum than milk by 72 h after. Chemically, the secreted fluid is free of lactose and fat (60% of the normal organic composition of milk) and its mineral composition and serum albumin concentration are similar to that of blood. The high plasmin activity at 96 h post treatment is consistent with the massive cell sloughing observed at this stage and indicate that the gland is undergoing intense remodeling.

Example 4

Treatment of Bovine Mastitis in a Single Udder

Eight cows suffering from mastitis caused by Actinomyces pyogenes were treated by intra mammary injections of 40 mg PP after successive milkings in the affected udder. In all 8 cases, the treated quarters of the gland dried up while the remaining 3 udders continued to produce milk at pretreatment levels while remaining uninfected. In 7 out of the 8 cases a complete recovery from mastitis was obtained a week after the beginning of the treatment as judged by (i) direct examination by a vet; (ii) a reduction of the somatic cell count to normal levels; and (iii) no evidence for bacteria in the gland by serological tests. In one case in which only partial improvement was observed the cow was treated by conventional treatment which involves cutting the nipple in order to get read of the infection product.

In addition to the trauma caused by this treatment, this quarter is lost forever in term of milk production. In contrast, treatment according to the present invention saves the treated quarter so that it will produce milk in subsequent lactation cycles.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications cited herein are incorporated by reference in their entirety.

REFERENCES CITED

1. Adamson, N. J. and Reynolds. C. E. 1995. Characterization of multiply phosphorylated peptides selectively precipitated from a pancreatic casein digest. J. Dairy Sci. 78, 2653–2659.
2. Andrews, A. T. 1983. Proteinases in normal bovine milk and their actions on caseins J. Dairy Res. 50, 45–55.
3. Andrews, A. T. 1978. The composition, structure and origin of proteose-peptone component 8F of bovine milk. Eur. J. Biochem. 90, 67–71.
4. Capuco, A. V. & Akers, R. M. 1999. Mammary involution in dairy animals. J. Mammary Gland Biol. Neoplasia 4: 137–144.
5. Caessens, P. W., Jr; Gruppen, H., Visser, S., vanAken, G. A. and Voragen, A. G. J. 1997. Plasmin hydrolysis of beta-casein: Foaming and emulsifying properties of the fractionated hydrolysate. J. Ag. Food Chem. 45: 2935–2941
6. Fleet, I. R. & Peaker, M. 1978. Mammary function and its control at the cessation in lactation in goats. J. Physiol. Lond. 279: 491–507.
7. Fitzgerald, R.J. 1998. Potential uses caseinophosphopeptides. Int. Dairy J. 8, 451–457.
8. Guerin, M. A. and Loizzi, R. F. 1978. Inhibition of mammary gland lactose secretion by colchicine and vincristine. A. J. Physiol. 234: C177–C180.
9. Ledbetter, M. L. and Lubin, M. 1977. Control of protein synthesis in human fibroplasts by intracellular potassium. Exp. Cell. Res. 105:223–226.
10. Li, M., Liu, X., Robinson, G., Bar-Peled, U., Wagner, K.-U., Young, W. S., Hennighausen, L. & Furth, P. A. 1997. Mammary-derived signals activate programmed cell death during the first stage of mammary gland involution. Proc. Natl. Acad. Sci. U.S.A. 94: 3425–3430.
11. Madara, J. L. 1987. Intestinal absorptive cell tight junction are linked to cytoskeleton Am. J. Physiol. 253: C171–C175.
12. Marti, A., Feng, Z. W., Altermatt, H. J. & Jaggi, R. 1997. Milk accumulation triggers apoptosis of mammary epithelial cells. Eur. J. Cell. Biol. 73: 158–165.
13. Nguyen, D-A, D. & Neville, M. C. 1998. Tight junction regulation in the mammary gland. J. Mammary Gland Biol. Neoplasia 3: 233–246.
14. Neville, M. C. & Peaker, M. 1981. Ionized calcium in milk and the integrity of the mammary epithelium in goats. J. Physiol. Lond. 313: 561–570.
15. Neville, M. C., Keller, R. P., Casey, C. & Allen, J. C. 1994. Calcium in human and bovine milk. J. Dairy Sci. 77: 1964–1975.

16. Nickerson, S. C., Smith, J. J. and Keenen, T. W. 1980. Role of microtubules in milk secretion-action of colchicine on microtubules and excoytosis of secretory vesicles in rat epithelial cells. Cell Tissue Res. 207: 361–376.
17. Patton, S. 1976a. Mechanism of secretion: Effects of colchicine and vicristine on composition and flow of milk in the goat. J. Dairy Sci. 50:1414–1419.
18. Patton, S. 1976b. Reversible suppression of milk secretion by concanvaline A. FEBS Lett. 71: 154–156.
19. Olivier, S. P & Sordillio, L. M. 1989. Approaches to the manipulation of mammary involution. J. Anim. Sci. 72:1647–1664.
20. Ossowski, L., Biggel, D. & Reich E. 1979. Mammary plasminogen activator: Correlation with involution, hormonal modulation and comparison between normal and neoplastic tissue. Cell 16, 929–940.
21. Pitelka, D. R., Taggart, B. N. and Hamamoto, S. T. 1983. Effects of extracellular calcium depletion on membrane topography and occluding junctions of mammary epithelial cells in culture. J. Ce. Biol. 96: 613–624.
22. Politis, I. 1996. Plasminogen activator system: Implication for mammary cell growth and involution J. Dairy Sci. 79, 1097–1107.
23. Quarrie, L. H., Addey, C. V. P. & Wilde, C. J. 1994. Local regulation of mammary apoptosis in the lactating goat. Biochem. Soc. Trans. 22:178S.
24. Quarrie, L. H., Addey, C. V. P. & Wilde, C. J. 1996. Programmed cell death during mammary involution induced by weaning, litter removal and milk stasis. J. Cell. Physiol. 168: 559–569.
25. Stelwagen, A., Davis, S. R., Farr, V. C., Prosser, C. G. & Sherlock, R. A. 1994. Mammary epithelial tight junction integrity and mammary blood flow during extended milking interval in goats. J. Dairy Sci. 77:426–432.
26. Stelwagen, A., Farr, V. C., Davis, S. R. & Prosser, C. G. & 1995. EGTA-induced disruption of epithelial cell tight junctions in the lactating caprine mammary gland. Am. J. Physiol. 273: R848–R855.
27. Stelwagen, A., Farr, V. C., MacFadden, H. A., Prosser, C. G. & Davis, S. R. 1997. Time course of milk accumulation-induced opening of mammary tight junctions, and blood clearance of milk components. Am. J. Physiol. 273: R379–R386.
28. Tatarczuch, C., Philip, C. & Lee, C. S. 1977. Involution of sheep mammary gland. J. Anat. 190: 405–416.
29. Wilde, C. J., Addey, C. V. P., Li, P. & Feming, D. G. 1977. Programmed cell death in bovine mammary tissue during lactation and involution. Exp. Physiol. 82: 943–953.
30. Wilde, C. J., Knight, C. H. & Flint, D. J. 1999. Control of milk secretion and apoptosis during mammary involution. J. Mammary Gland Biol. Neoplasia 4: 129–136.

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 20
      (B) TYPE: amino acid
      (C) STRANDEDNESS: single
      (D) TOPOLOGY: linear    (xi) SEQUENCE DESCRIPTION: SEQ ID NO: 1:

Gln Met Glu Ala Glu Xaa Ile Xaa Xaa Glu G lu Ile Val Pro Asn
               5                      10                 15

Xaa Val Glu Gln Lys
          20

(2) INFORMATION FOR SEQ ID NO: 2:

(i) SEQUENCE CHARACTERISTICS:
      (A) LENGTH: 8
      (B) TYPE: amino acid
      (C) STRANDEDNESS: single
      (D) TOPOLOGY: linear    (xi) SEQUENCE DESCRIPTION: SEQ ID NO: 2:

Val Pro Asn Xaa Ala Glu Glu Arg
             5

(2) INFORMATION FOR SEQ ID NO: 3:

(i) SEQUENCE CHARACTERISTICS:
      (A) LENGTH: 12
      (B) TYPE: amino acid
      (C) STRANDEDNESS: single

```
        (D) TOPOLOGY: linear (xi) SEQUENCE DESCRIPTION: SEQ ID NO: 3:

Glu His Val Ser Xaa Xaa Glu Glu Ile Xaa G ln Glu
                5                  10

(2) INFORMATION FOR SEQ ID NO: 4:

(i) SEQUENCE CHARACTERISTICS:
        (A) LENGTH: 6
        (B) TYPE: amino acid
        (C) STRANDEDNESS: single
        (D) TOPOLOGY: linear (xi) SEQUENCE DESCRIPTION: SEQ ID NO: 4:

Asn Pro Xaa Lys Glu Asn
                5

(2) INFORMATION FOR SEQ ID NO: 5:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 5:

Gly Xaa Xaa Xaa Glu Glu Xaa Ala Glu Val
                5                  10

(2) INFORMATION FOR SEQ ID NO: 6:

(i) SEQUENCE CHARACTERISTICS:
        (A) LENGTH: 21
        (B) TYPE: amino acid
        (C) STRANDEDNESS: single
        (D) TOPOLOGY: linear (xi) SEQUENCE DESCRIPTION: SEQ ID NO: 6:

Gln Leu Xaa Thr Xaa Glu Glu Asn Ser Lys L ys Thr Val Asp Met
                5                  10                  15

Glu Xaa Thr Glu Val Phe
                20

(2) INFORMATION FOR SEQ ID NO: 7:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 7:

Ile Val Glu Xaa Xaa Xaa Glu Glu Ser Ile L ys
                5                  10
```

What is claimed is:

1. A pharmaceutical composition for changing the physiologic status in a mammary gland of a lactating animal, the pharmaceutical composition comprising, as an active ingredient, an effective amount of a protein capable of causing a change in the physiologic status of a mammary gland and a pharmaceutically acceptable carrier, wherein said change in the physiologic status of a mammary gland is selected from the group consisting of transient cessation of milk production, persistent cessation of milk production, prevention of infection and reversal of infection.

2. The pharmaceutical composition of claim 1, wherein said protein is selected from the group of proteins consisting of casein derived proteose-peptones and synthetic phosphopeptides.

3. The pharmaceutical composition of claim 1, wherein said effective amount of said protein is administered as a single dose of protein in combination with cessation of milking so as to cause persistent cessation of milk production in the mammary gland of the lactating animal.

4. A method of changing the physiologic status in a mammary gland of a lactating animal, the method comprising the step of administering a protein into the mammary gland of the lactating animal to cause a change in the physiologic status, wherein said change in the physiologic status is selected from the group consisting of transient cessation of milk production, persistent cessation of milk production, prevention of infection and reversal of infection.

5. The method of claim 4, wherein said step of administering said protein into the mammary gland of the lactating animal is effected by injecting said protein into a teat canal of the mammary gland of the lactating animal.

6. The method of claim 4, wherein said protein is selected from the group of proteins consisting of casein derived proteose-peptones and synthetic phosphopeptides.

7. The method of claim 4, wherein a single dose of said protein in combination with cessation of milking induces involution and results in persistent cessation of milk production in the mammary gland of the lactating animal.

8. The method of claim 4, wherein the animal is a live-stock animal.

9. The method of claim 4, wherein the animal is selected from the group of animals consisting of cow, goat, sheep, lama, human, camel, donkey, pig, dog and cat.

* * * * *